(12) United States Patent
Okamura et al.

(10) Patent No.: US 7,749,722 B2
(45) Date of Patent: Jul. 6, 2010

(54) MEASURING METHOD USING WHOLE BLOOD

(75) Inventors: Yoshikazu Okamura, Tokyo (JP); Takashi Kurihara, Tokyo (JP); Hiroyuki Yokoi, Tokyo (JP); Junichi Ogawa, Tokyo (JP)

(73) Assignee: Mitsubishi Kagaku Istron, Inc., Tokyo (JP)

( * ) Notice: Subject to any disclaimer, the term of this patent is extended or adjusted under 35 U.S.C. 154(b) by 468 days.

(21) Appl. No.: 11/300,867

(22) Filed: Dec. 15, 2005

(65) Prior Publication Data

US 2007/0141645 A1 Jun. 21, 2007

(51) Int. Cl.
*G01N 33/53* (2006.01)
*G01N 1/00* (2006.01)

(52) U.S. Cl. .............................. 435/7.9; 435/4; 435/7.1; 435/7.72; 435/7.92; 435/7.94; 435/287.2; 436/518; 436/523; 436/524; 436/526; 436/537; 436/538; 436/175; 436/177

(58) Field of Classification Search ............. 435/4, 435/7.2, 7.9, 7.92, 7.94, 21, 7.1, 7.72, 287.2; 436/517, 518, 523, 524–530, 537, 538, 46, 436/56, 166, 172, 175, 177
See application file for complete search history.

(56) References Cited

U.S. PATENT DOCUMENTS

| | | | |
|---|---|---|---|
| 5,135,847 A | 8/1992 | Hoke | 435/5 |
| 5,948,630 A * | 9/1999 | Singh et al. | 435/21 |
| 6,143,510 A | 11/2000 | Hoshino et al. | 435/7.94 |
| 6,280,618 B2 * | 8/2001 | Watkins et al. | 210/222 |

FOREIGN PATENT DOCUMENTS

| | | | |
|---|---|---|---|
| EP | 0 530 490 | * | 3/1993 |
| EP | 0530490 | | 3/1993 |
| JP | 2000-193666 | | 7/2000 |
| WO | WO 94/19691 | | 9/1994 |
| WO | 96/04558 | | 2/1996 |
| WO | 01/96868 | | 12/2001 |

OTHER PUBLICATIONS

Kricka L.J., Strategies for immunoassay, Pure and Applied Chemistry 68 (10): 1825-1830 (Oct. 1996).*
Tumosa et al., Fluorescent EIA screening of monoclonal antibodies to cell surface antigens, Journal of immunological methods, 116 (1): 59-63 (Jan. 6, 1989).*

* cited by examiner

*Primary Examiner*—Gailene R Gabel
(74) *Attorney, Agent, or Firm*—Heslin Rothenberg Farley & Mesiti P.C.

(57) ABSTRACT

A method for measuring an analyte in a whole blood sample comprising the steps of (1) bringing the whole blood sample into contact with a first substance which is carried on an insoluble carrier and specifically binds to the analyte to be measured and a second substance which is labeled with an alkaline phosphatase and specifically binds to the analyte to be measured, and (2) measuring a resulting complex on the basis of an enzyme reaction of the alkaline phosphatase, the measuring step (2) being carried out in the presence of an inhibitor of endogenous alkaline phosphatases, is disclosed.

18 Claims, 2 Drawing Sheets

MEASURING METHOD USING WHOLE BLOOD

BACKGROUND OF THE INVENTION

1. Field of the Invention

The present invention relates to a measuring method in which whole blood is used as a sample. More particularly, the present invention relates to a method for measuring an analyte contained in a whole blood sample (i.e., a sample comprising whole blood) using an inhibitor of endogenous alkaline phosphatases.

2. Description of the Related Art

An alkaline phosphatase is widely used in labeling an antibody, for example, in an enzyme immunoassay or an enzyme immunostaining. Various alkaline phosphatases widely exist in an animal body. Therefore, when a sample collected from an animal such as a human is used, one or more alkaline phosphatases contained in the sample (hereinafter sometimes referred to as "endogenous alkaline phosphatases") often affects a result of an enzyme immunoassay or an enzyme immunostaining.

To avoid such an effect, for example, an immunoassay kit using an inhibitor of endogenous alkaline phosphatases [see, for example, Japanese Examined Patent Publication (Kokoku) No. 8-20446], a washing composition comprising an inhibitor of endogenous alkaline phosphatases and a surfactant to reduce a background (see, for example, Japanese Patent No. 3350730), and a method using an inactivated alkaline phosphatase as an absorbent [see, for example, Japanese Unexamined Patent Publication (Kokai) No. 2000-193666] were reported. The term "inhibitor of endogenous alkaline phosphatases" as used herein means an inhibitor which does not inhibit an alkaline phosphatase used as a label but inhibits only endogenous alkaline phosphatases, on the basis of the fact that there are plural alkaline phosphatases having different properties.

In the field of POCT (Point of Care Testing) or the like regarded in a clinical laboratory test, a compact and convenient apparatus or an examining method in which a doctor or a nurse rapidly carry out an examination is desired. A measuring apparatus in which collected whole blood can be used directly without a pretreatment, to accomplish a rapid examination, is desired in the POCT field. If whole blood can be used as a sample, an examination can be carried out more rapidly, those other than an expert can operate the apparatus, and a large apparatus such as a centrifuge is not necessary.

However, when whole blood is used as a sample, the sample contains many interferents, and therefore, an increased background often reduces the accuracy of the measurement, or it is often difficult to measure a small amount of analyte to be analyzed. In particular, the increased background sometimes causes serious problems in a clinical laboratory test, for example, inaccurate measured values or a false decision. No methods to avoid the problems are established. For example, a chemiluminescent immunoassay using an alkaline phosphatase and a sensitive chemiluminescent substrate for the alkaline phosphatase is being developed. When whole blood is used as a sample in such a high-sensitive assay, an extremely increased background reduces the accuracy of the measurement. As factors causing the increased background, for example, an inhibition by one or more interferents, nonspecific binding of interferent protein such as a blood cell membrane, or the like is considered, but the details are unclear. To resolve the problems, a sensitive and high-precision measuring method using a whole blood sample is desired.

SUMMARY OF THE INVENTION

An object of the present invention is to provide a measuring method using a whole blood sample.

In a conventional measuring method using a whole blood sample, an increased background specific to the whole blood sample is observed. The present inventors have conducted intensive studies and, as a result, found that such a specific background was remarkably suppressed when an enzyme reaction was carried out in the presence of an inhibitor of endogenous alkaline phosphatases. The present invention is based on that finding.

The present invention relates to

[1] a method for measuring an analyte in a whole blood sample comprising the steps of:

(1) bringing the whole blood sample into contact with a first substance which is carried on an insoluble carrier and specifically binds to the analyte to be measured and a second substance which is labeled with an alkaline phosphatase and specifically binds to the analyte to be measured, and (2) measuring a resulting complex on the basis of an enzyme reaction of the alkaline phosphatase, the measuring step (2) being carried out in the presence of an inhibitor of an endogenous alkaline phosphatase,

[2] the method of [1], wherein the inhibitor of an endogenous alkaline phosphatase is a compound selected from the group consisting of levamisole, tetramisole, homoarginine, and a derivative thereof,

[3] the method of [1] or [2], wherein the inhibitor of an endogenous alkaline phosphatase is contained in a solution of a substrate for the alkaline phosphatase used as the label.

[4] the method of any one of [1] to [3], wherein the substrate is a 1,2-dioxetane-based compound or an acridan-phosphate-based compound,

[5] the method of any one of [1] to [4], wherein the endogenous alkaline phosphatase is derived from a blood cell,

[6] a reagent kit for measuring an analyte in a whole blood sample, comprising (1) a first substance which is carried on an insoluble carrier and specifically binds to the analyte to be measured, (2) a second substance which is labeled with an alkaline phosphatase and specifically binds to the analyte to be measured, and (3) an inhibitor of an endogenous alkaline phosphatase, and

[7] the reagent kit of [6], wherein the inhibitor of an endogenous alkaline phosphatase is contained in a solution of a substrate for the alkaline phosphatase used as the label.

According to the present invention, even when an alkaline phosphatase and a sensitive chemiluminescent substrate for the alkaline phosphatase are used in a measuring method using a whole blood sample, a background can be lowered to accomplish a high-precision measurement.

DESCRIPTION OF THE PREFERRED

The present invention now will be further illustrated.

1. Measuring Method of the Present Invention

The measuring method of the present invention is characterized by comprising the steps of:

(1) bringing a whole blood sample into contact with a first substance which is carried on an insoluble carrier and specifically binds to an analyte to be measured and a second substance which is labeled with an alkaline phosphatase and specifically binds to the analyte to be measured, and (2) measuring a resulting complex on the basis of an enzyme reaction of the alkaline phosphatase, and carrying out at least the measuring step (2) in the presence of an inhibitor of endogenous alkaline phosphatases.

(1) Sample and Analyte to be Measured

As the whole blood sample which may be applied to the measuring method of the present invention, whole blood per se may be used. The term "whole blood" as used herein means blood per se collected from a subject such as a human and containing unseparated blood cells. Further, a sample obtained by diluting the whole blood with an appropriate buffer or the like, and/or by adding an additive, such as an anticoagulant or a protease inhibitor, may be used as the whole blood sample.

The buffer for diluting whole blood is not particularly, limited, so long as it does not hemolyze blood cells contained in the whole blood and does not modify various components contained in the whole blood. As the buffer, for example, a solution adjusted to a physiological pH, a physiological osmotic pressure, a physiological salt concentration, or the like, such as a phosphate-buffered saline (PBS), a physiological saline, or a physiological salt solution, may be used. Further, an appropriate volume of a solution other than the adjusted solutions may be added to the buffer, so long as it does not affect blood cells or other components. When whole blood contains an analyte to be measured in a very small amount, it is preferable to use whole blood per se or a mixture of whole blood with a small amount of other components.

As the anticoagulant, there may be mentioned, for example, heparin, EDTA, or citrate. The anticoagulant may be preferably used by previously adding it to a blood collection tube or the like when blood is collected from a subject such as a human.

In the present invention, an analyte contained in such a sample may be measured. As the analyte to be measured, there may be mentioned, for example, an immunological substance, a biological substance, or a molecular biological substance, such as an antigen, an antibody, a protein, a ligand, an enzyme, a substrate, a DNA, a vector DNA, an RNA, or a plasmid. More particularly, there may be mentioned, for example, a hepatitis B virus surface antigen (HBsAg), a hepatitis C virus antibody or antigen, a human immunodeficiency virus (HIV) antibody, a human T cell leukemia virus-1 (HTLV-1) antibody, or a Treponema pallidum (TP) antibody. Further, there may be mentioned, for example, various myocardial markers [such as creatine kinase (CKMB), myoglobin, or troponin], D-dimer, a fibrin degradation product (FDP), C-reactive protein (CRP), carbohydrate antigen 19-9 (CA19-9), carcinoembryonic antigen (CEA), carbohydrate antigen 125 (CA125), prostate-specific antigen (PSA), various hormones, or a serum protein.

(2) Measuring Method

In the present invention, an analyte exemplified as above is measured by using a first substance which specifically binds to the analyte to be measured and a second substance which is labeled with an alkaline phosphatase and specifically binds to the analyte to be measured. As a combination of the analyte to be measured and the first or second substance, there may be mentioned, for example, an antibody and an antigen, an antibody and an antibody, a protein and a ligand, a sugar chain and a lectin, or nucleic acids having complementary sequences. In this connection, the order of substances in each combination is not particularly limited, and any substance may be used as the analyte to be measured or the first or second substance. Among the combinations, the combination of an antibody and an antigen, or the combination of an antibody and an antibody is preferable, and the combination of an antibody and an antigen is more preferable. The term "specifically bind" as used herein means a substance that specifically binds biochemically to form a reaction product.

The measuring method of the present invention is a heterogeneous assay using an insoluble carrier coated with the first substance which specifically binds to an analyte to be measured and the second substance which is labeled with an alkaline phosphatase and specifically binds to the analyte to be measured. The method is not particularly limited, so long as it comprises the step of reacting the analyte to be measured contained in a whole blood sample with the first and second substances (hereinafter referred to as the reacting step), and the step of measuring the generated reaction product (hereinafter referred to as the measuring step). For example, the first substance which is carried on an insoluble carrier and specifically binds to the analyte to be measured and the second substance which specifically binds to the analyte to be measured may be added to a whole blood sample to carry out the reaction. The first and second substances and the analyte to be measured may be reacted simultaneously or one after the other, i.e., in turn, preferably in turn. When the reactions in the reacting step are carried out in turn, it is preferred that the analyte to be measured is reacted with the first substance to form the first reaction product (first reacting step), and then a B/F separation (first separating step) is carried out. Further, it is preferred that the B/F-separated first reaction product is reacted with the second substance to form the second reaction product (second reacting step), and then a B/F separation (second separating step) is carried out. These procedures may improve the sensitivity of the measurement. The reaction conditions in each step may be appropriately selected in accordance with the combination of the analyte to be measured and the first and second substances which specifically bind thereto.

For example, when an antigen contained in whole blood is measured, a whole blood sample may be mixed with an insoluble carrier coated with an antibody (first substance) specific to the antigen and another antibody (second substance) labeled with an alkaline phosphatase to form an immunocomplex, unreacted antibodies and antigen may be removed by washing (B/F separation), and an amount of alkaline phosphatase which binds to the insoluble carrier may be measured. More particularly, for example, a whole blood sample and magnetic particles (insoluble carrier) coated with the first antibody are added to a reaction vessel, and the mixture is stirred to carry out an antigen-antibody reaction at an appropriate temperature for an appropriate period. After the reaction, unreacted substances are removed from the reaction vessel by a magnetic B/F separation. The second antibody labeled with alkaline phosphatase is added to the reaction vessel to carry out a reaction at an appropriate temperature for an appropriate period. Any unreacted antibody is removed from the reaction vessel by a magnetic B/F separation. An amount of alkaline phosphatase contained in the generated reaction product is measured to determine an amount of the analyte to be measured.

The insoluble carrier is not particularly limited, so long as it is substantially insoluble to various solutions used in the measurement. For example, a magnetic particle, a macromolecule (such as polystyrene) or a latex thereof, gelatin, or a liposome may be preferably used. To obtain a rapid and convenient B/F separation, a more preferred insoluble carrier is a magnetic particle, more particularly, a microparticle of, for example, a metal (such as $Fe_3O_4$, $Fe_2O_3$, various ferrites, iron, manganese, nickel, cobalt, or chromium) or an alloy (such as cobalt, nickel, or manganese). The magnetic particle may be preferably used in a core-shell form in which the core portion is the magnetic particle and the shell portion is, for example, gelatin, a liposome, or a latex of macromolecule such as polystyrene, or immobilized on the surface thereof.

A particle size of the insoluble carrier is not particularly limited, so long as a B/F separation may be carried out accurately. The lower limit of the particle size is 0.05 µm, preferably 0.1 µm. When the particle size is less than the lower limit, sometimes a sufficient separation efficiency is not obtained and the particles tend to agglutinate. The upper limit of the particle size is 10 µm, preferably 4 µm, more preferably 3 µm. When the particle size is more than the upper limit, the particles tend to precipitate. The particle size may be selected between the lower and upper limits, and may be generally 0.05 to 10 µm, preferably 0.05 to 4 µm, more preferably 0.1 to 4 µm, most preferably 1 to 3 µm.

The first substance which specifically binds to an analyte to be measured may be carried or coated on the insoluble carrier by a conventional method such as a chemically binding method or a physical adsorption method.

The B/F separation using the obtained insoluble carrier can be carried out by, for example, a filter method, a two antibody sandwich method, or a precipitation method. When a magnetic particle is used as the insoluble carrier, the B/F separation may be carried out rapidly and conveniently by utilizing a magnetic force of, for example, a permanent magnet or an electromagnet.

The step of measuring an amount of alkaline phosphatase contained in the reacting product is based on an enzyme reaction of alkaline phosphatase. That is, an amount of alkaline phosphatase may be determined by carrying out the enzyme reaction of alkaline phosphatase and measuring an amount of a signal (for example, luminescence, coloring, or fluorescence) generated from a substrate. In the measuring method of the present invention, a method for measuring an amount of luminescence (hereinafter referred to as chemiluminescent method) is preferable. A measuring method and an apparatus used therein may be appropriately selected in accordance with a substrate for alkaline phosphatase.

When a chemiluminescent method is used in the measuring step, a 1,2-dioxetane-based compound or an acridan-phosphate-based compound may be preferably used as the substrate of alkaline phosphatase. As a chemiluminescent substrate derived from 1,2-dioxetane, for example, disodium 3-(4-methoxyspiro {1,2-dioxetane-3,2'-tricyclo [$3.3.1.1^{3,7}$] decan}-4-yl)phenyl phosphate (AMPPD) or disodium 2-chloro-5-(4-methoxyspiro{1,2-dioxetane-3,2'-(5'-chloro) tricyclo[$3.3.1.1^{3,7}$]decan}-4-yl)-1-phenylphosphate (CDP-Star: Tropics) may be preferably used. Further, as an acridan-phosphate-based compound, for example, APS-5 (Lumigen) may be preferably used.

When a coloring method is used, for example, 4-nitrophenylphosphate may be used. When a fluorescent method is used, for example, 4-methylumbelliferylphosphate may be used.

(3) Measuring Step Using Inhibitor of Endogenous Alkaline Phosphatases

The measuring method of the present invention is characterized by carrying out the measuring step in the presence of an inhibitor of endogenous alkaline phosphatases.

In a conventional measuring method using an alkaline phosphatase as a label for the second substance, when whole blood is used as a sample, it is often difficult to obtain an accurate result because of an increased background, in comparison with a case of a plasma or serum sample. The problem is more remarkable in a chemiluminescent assay using a sensitive substrate. The present inventors have conducted intensive studies and, as a result, found the increased background observed in the case of a whole blood sample was caused by a large amount of alkaline phosphatase contained in blood cells. Further, the present inventors found that the increased background caused by the alkaline phosphatase derived from blood cells was remarkably suppressed by carrying out the measuring step in the presence of an inhibitor of endogenous alkaline phosphatases, and that an accurate measurement was accomplished. The present invention can resolve the above problem, and exhibits an advantageous effect in that even a whole blood sample can be measured sensitively and accurately.

The term "endogenous alkaline phosphatase(s)" as used herein means an alkaline phosphatase, originally contained in a sample, other than the alkaline phosphatase used as the label. It is known that alkaline phosphatases include plural isoforms. In the present invention, an inhibitor which does not substantially inhibit the alkaline phosphatase used as the label but inhibits only endogenous alkaline phosphatases is used, on the basis of differences among the isoforms. The expression "not substantially inhibit" means that a function as the label in the enzyme reaction is not substantially inhibited, to provide an accurate result of the measurement.

The isoforms of alkaline phosphatases include, for example, an alkaline phosphatase derived from a liver, kidney, bladder, ovary, salivary gland, bone, neutrophil, or lymphocyte (tissue-type), an alkaline phosphatase derived from the small intestine (small-intestine-type), and an alkaline phosphatase derived from the placenta (placenta-type). For example, when whole blood is used as a sample, tissue-type endogenous alkaline phosphatases derived from blood cells are contained in the sample, and thus, an inhibitor which inhibits the activity thereof may be used. Preferably, a small-intestine-type alkaline phosphatase is used as the label, and an inhibitor of a tissue-type alkaline phosphatase is used.

As the inhibitor of endogenous alkaline phosphatases, there may be mentioned, for example, levamisole, tetramisole, homoarginine, L-phenylalanine, or a derivative thereof. Levamisole, tetramisole, or homoarginine may be preferably used, because of the activity of inhibiting tissue-type and/or placenta-type alkaline phosphatase(s). Levamisole exhibits an extreme specificity, and thus, is most preferable. In the present invention, a combination of plural inhibitors may be used. The inhibitors are known compounds, and thus, are commercially available, or may be easily synthesized.

A concentration of the inhibitor to be added is not particularly limited, so long as it can inhibit the endogenous alkaline phosphatase activity and does not affect a result of the measurement. When a large amount of the inhibitor is added, the alkaline phosphatase used as the label is sometimes adversely affected. The upper limit is preferably less than such a concentration.

A concentration of the inhibitor to be added may be appropriately selected, for example, in accordance with guidance that a background is low enough to not affect the measurement or judgment or is as low as that of a plasma or serum sample. More particularly, when a sample containing endogenous alkaline phosphatases is measured by a conventional method, except that the label is not used, a background is increased by reacting a substrate with the endogenous alkaline phosphatases. To this measuring system, an inhibitor such as levamisole is added, so that the background is lowered without an affect on the measurement or judgment, to determine the inhibitor concentration. Alternatively, the background is compared to a background obtained by measuring a plasma or serum sample to determine the inhibitor concentration, in accordance with the guidance that the former is as low as the latter.

Further, the inhibitor concentration may be determined by an amount of a signal generated from the enzyme reaction of the alkaline phosphatase used as the label and the substrate thereof as an index. For example, when an amount of a signal derived from a whole blood sample in the presence of a certain amount of the inhibitor is the same as that derived from a plasma or serum sample, a buffer, or the like, the amount of the inhibitor may be used as an appropriate concentration which can suppress the background caused by the endogenous alkaline phosphatases derived from blood cells in whole blood.

When levamisole is used as the inhibitor, the lower limit is generally 0.01 mM, preferably 0.1 mM, more preferably 0.2 mM, and the upper limit is generally 50 mM, preferably 5 mM, more preferably 1 mM, as the final concentration thereof in the enzyme reaction. The inhibitor concentration may be selected between the lower and upper limits. For example, the concentration of levamisole is generally 0.01 to 50 mM, preferably 0.1 to 5 mM, more preferably 0.2 to 1 mM. In view of the stability of a substrate for the alkaline phosphatase used as the label, the concentration of levamisole in the enzyme reaction is preferably 0.1 to 1 mM, more preferably 0.2 to 0.8 mM, most preferably 0.2 to 0.6 mM. The method for adding the inhibitor is not particularly limited, so long as at least the measuring step (i.e., the reaction of the alkaline phosphatase used as the label with the substrate) is carried out in the presence of the inhibitor.

The inhibitor may be added to, for example, a substrate solution, a reaction liquid, or a B/F washing liquid, preferably a substrate solution. In the case of a chemiluminescent method using a sensitive substrate, it is most preferable to add the inhibitor to a substrate solution. The addition of the inhibitor to a substrate solution can efficiently suppress the reaction of the sensitive substrate with endogenous alkaline phosphatases.

Because it is considered that an increased background is mainly caused by endogenous alkaline phosphatases derived from blood cells in whole blood, it is preferable that hemolysis of a sample is substantially avoided in the present invention. That is, it is preferable that a conventional method for avoiding hemolysis is used in the present invention. The expression "hemolysis is substantially avoided" as used herein means that hemolysis does not occur in a whole blood sample, or that it does not affect the measurement when it does occur.

As the method for avoiding hemolysis, there may be mentioned, for example, an addition of a surfactant capable of avoiding substantial hemolysis, an adjustment by an isotonic liquid, an addition of a magnesium ion or the like for avoiding disruption of a cell nucleus, or a combination thereof. In the addition of a surfactant capable of avoiding substantial hemolysis, an appropriate surfactant is added to a reaction system at an appropriate concentration, so that it does not substantially inhibit the reaction of an analyte to be measured and the first and second substances specific thereto, and may avoid affecting reactions caused by components contained in the reaction system, without substantial hemolysis. As the surfactant, for example, a polyoxyethylene sorbitan-based surfactant or a sulfobetaine-based surfactant may be used. The method is disclosed in, for example, WO02/73203 in detail.

These above-mentioned methods may be appropriately combined to enhance the effects of the present invention and carry out the measurement with a high accuracy.

When whole blood is used as a sample, a hematocrit compensation after the measurement is generally required. A hematocrit value is generally approximately 40 to 50% in the blood from a male and approximately 35 to 45% in that from a female. In the case of a qualitative measurement such as a positive-negative judgment of an infection disease, a hematocrit compensation is not important, and thus, it is not practically necessary to measure a hematocrit value of each sample. When the hematocrit value is obtained, a result with high accuracy may be obtained by the hematocrit compensation [(measured value)×100/(100−(hematocrit value)(%))].

2. Reagent Kit of the Present Invention

The reagent kit of the present invention is characterized by comprising at least an inhibitor of endogenous alkaline phosphatases, and may be used in the measuring method of the present invention.

The constitution of the reagent kit of the present invention is the same as a conventional kit for measuring an analyte contained in whole blood, a plasma, or a serum, except that the inhibitor of endogenous alkaline phosphatases is contained. That is, the reagent kit of the present invention comprises the first substance which is carried on an insoluble carrier and specifically binds to the analyte to be measured, and the second substance which is labeled with an alkaline phosphatase and specifically binds to the analyte to be measured, and may be used in the measuring method of the present invention. The reagent kit of the present invention may further comprise, for example, a diluting liquid, a substrate solution, a washing liquid, or a liquid for stopping a reaction. The inhibitor of endogenous alkaline phosphatases is preferably added to the substrate solution. In the substrate (preferably a chemiluminescent substrate, more preferably AMPPD or CDP-Star) solution containing the inhibitor (preferably levamisole) of endogenous alkaline phosphatases, a concentration of the inhibitor may be preferably 0.1 to 1 mM, more preferably 0.2 to 0.8 mM, most preferably 0.2 to 0.6 mM. When the inhibitor of endogenous alkaline phosphatases is contained in the substrate solution at a low concentration within the above range, the stability of the substrate may be improved.

According to the reagent kit of the present invention, the measuring method of the present invention can be carried out rapidly, conveniently, and accurately.

The measuring method of the present invention may be carried out using, for example, a conventional automated analyzer or a cartridge contained in the automated analyzer, disclosed in, for example, WO01/84152, Japanese Patent No.

3115501, or Japanese Unexamined Patent Publication (Kokai) No. 11-316226. Preferably, the reagent kit of the present invention may be packaged in a cartridge for an automated analysis, and used in such an automated analyzer. The measuring method and the reagent kit of the present invention may be used together with an automated analyzer and/or a cartridge to accomplish a rapid, convenient, and accurate measurement.

EXAMPLES

The present invention will now be further illustrated by, but is by no means limited to, the following Examples.

Example 1

Analysis of Factor Effecting Enzyme Immunoassay in Whole Blood

It was reported that a background was remarkably increased when whole blood was used as a sample in a conventional enzyme immunoassay using an antibody labeled with an alkaline phosphatase and a sensitive substrate thereof, in comparison with cases using a plasma or a serum as a sample. The following experiment was carried out to clarify the cause.

As samples, five samples obtained from healthy persons were used. When each sample was collected, heparin was added. From each sample, a whole blood sample (i.e., whole blood per se), a plasma sample (obtained by centrifuging whole blood), and a hemolysis sample (obtained by adding to whole blood an agent for hemolysis) were prepared.

Each sample was measured using a reagent kit for measuring cardiac troponin I (cTnI). The kit contained a solution of the first antibody specific to cTnI (a solution of magnetic particles), a solution of the labeled second antibody, a B/F washing liquid, a substrate solution, and the like, and was packaged in a cartridge applicable to an automated immunoanalyzer described below. In this example, a buffer not containing a labeled antibody was used, instead of the solution of the second antibody labeled with an alkaline phosphatase (hereinafter referred to as "ALP"). The measurement was carried out using an automated immunoanalyzer for an immunoassay using magnetic particles, as disclosed in Japanese Patent No. 3115501. In the analyzer, an efficient B/F separation can be magnetically carried out in a tip arranged as an aspiration/deliver line, and thus, it shows a high efficiency in washing. The measuring step in the analyzer will be described below.

A chemiluminescent substrate CDP-Star (Tropics) was used as a substrate. A count of luminescence detected by a photomultiplier tube (PMT) was regarded as a result of the measurement.

Measurement by Automated Immunoanalyzer

Each cartridge for an automatic measurement was filled with each sample, a liquid for diluting a sample, the solution of magnetic particles (coated with the first antibody), the washing liquid for B/F separation, the solution of the second antibody, the substrate solution, and the like, and set to the automated analyzer. The following steps were carried out in accordance with a normal procedure:

(1) The sample solution, the solution of magnetic particles, and the solution of the second antibody, previously adjusted to predetermined dilutions with the diluting liquid, were mixed to generate an immunocomplex by an antigen-antibody reaction.

(2) A B/F separation was carried out to remove unreacted substances as follows. The resulting reaction liquid was aspirated into the tip arranged as a line for aspirating a solution, and the magnetic particles were trapped by contact with a magnet on the outer wall of the tip. The solution was delivered from the tip while trapping the magnetic particles on the inner wall of the tip. After the separation, the washing liquid for the B/F separation filled in another reaction vessel was aspirated and delivered to wash the magnetic particles in the tip.

(3) The magnet was separated from the outer wall of the tip. The substrate solution was aspirated and delivered to disperse the magnetic particles trapped on the inner wall of the tip and carry out an enzyme reaction.

(4) An amount of luminescence was measured by PMT.

The result is shown in Table 1.

TABLE 1

| Sample | Hemolysis | Sample No. | | | | |
| --- | --- | --- | --- | --- | --- | --- |
| | | 1 | 2 | 3 | 4 | 5 |
| Whole blood | − | 227 | 802 | 3202 | 255 | 336 |
| | + | 397 | 1471 | 10034 | 346 | 466 |
| Plasma | − | 218 | 218 | 390 | 195 | 178 |
| | + | 248 | 194 | 200 | 194 | 195 |

As a result, most whole blood samples showed a higher luminescent count in comparison with the corresponding plasma samples. The result was more remarkable in the hemolysis samples.

Further, although the buffer not containing ALP was used instead of the ALP-labeled antibody generally used as the second antibody solution, an increased background was observed. The result suggests that an endogenous ALP may cause the increased background.

Example 2

Identification of Component Effecting Enzyme Immunoassay in Whole Blood

Because the result obtained in Example 1 suggests that an endogenous ALP contained in whole blood may affect an enzyme immunoassay, the factor was identified in this example.

As samples, a whole blood sample and a hemolysis sample obtained by hemolysing whole blood with an agent for hemolysis were used. Each sample was centrifuged at 3000 rpm for 10 minutes to fractionate erythrocytes and leukocytes in accordance with a conventional method. A plasma obtained by centrifugation was mixed with (1) a physiological saline, (2) the leukocytes, or (3) the erythrocytes at the ratio of 1:1.

The resulting 6 samples were measured using the automated immunoanalyzer and the reagent kit for measuring cTnI, as described in Example 1. The result is shown in Table 2.

TABLE 2

| Hemolysis | Plasma + Saline | Plasma + Leukocytes | Plasma + Erythrocytes |
| --- | --- | --- | --- |
| − | 831 | 2170 | 1175 |
| + | 1009 | 19794 | 1332 |

As a result, it was found that an endogenous ALP contained in leukocytes caused the increased background. Further, the increase was enhanced by hemolysis.

Next, an effect of filtration was examined by using a whole blood sample. In this connection, it was previously confirmed that an ALP value became high when the whole blood sample was hemolyzed. A filtrate obtained by filtering the whole blood sample was red and transparent. The filtration was carried out using a syringe equipped with a filter unit having a pore size of 0.8 μm (MILLEX-PF: Millipore) or 1.2 μm (Minisart: Sartorius), in accordance with a conventional method. The obtained hemolyzed samples after filtration were measured using the automated immunoanalyzer and the reagent kit for measuring cTnI, as described above, except that the ALP-labeled antibody was used as the second antibody. The result (count of luminescence) is shown in Table 3.

TABLE 3

|  | Filtration | | |
| --- | --- | --- | --- |
|  | Not treated | 1.2 μm | 0.8 μm |
| Count | 105721 | 591 | 544 |

As a result, a decreased background was remarkably observed by filtrating the whole blood sample. It is most unlikely that ALP per se is filtered out through the membrane having such a pore size, and thus, it is considered that most endogenous ALP increased in the reaction liquid by hemolysis may bind to a blood cell membrane or the like. Accordingly, it is considered that the endogenous ALP which non-specifically binds to, for example, a blood cell membrane or magnetic particles, and not removed by a washing treatment with a conventional washing liquid for a B/F separation causes the increased background in an enzyme immunoassay using magnetic particles.

As described above, the problem of the increased background occurs when a whole blood sample is used. It is difficult to completely avoid the homolysis of a whole blood sample, and it is considered that an inhibition of the endogenous ALP will effectively solve the problem.

Example 3

Examination of Inhibitory Effect of Levamisole on Endogenous ALP in Whole Blood

Levamisole widely used as an inhibitor of an endogenous ALP in an immunostaining or an immunological reaction was used to examine whether or not the increased background caused by an endogenous ALP in an whole blood sample, as clarified in Examples 1 and 2, can be suppressed.

The whole blood sample showing a high background in Example 1 was used as a whole blood negative control, and a plasma obtained by centrifuging the whole blood sample was used as a plasma negative control. Further, a sample obtained by adding a commercially available cTnI (10 ng/mL) to the whole blood sample was used as a whole blood positive control, and a plasma obtained by centrifuging the whole blood positive control was used as a plasma positive control. The obtained 4 samples were measured using the automated immunoanalyzer and the reagent kit for measuring cTnI, as described in Example 1 or 2, except that the ALP-labeled antibody was used as the second antibody.

Levamisole (SIGMA) was used to examine an inhibitory effect on an endogenous ALP. Levamisole was added to the solution of magnetic particles, the substrate solution, or both thereof at the final concentration of 0.2 mM. When levamisole was added to the solution of magnetic particles, the inhibitor acted in the measuring step (1) of the automated immunoanalyzer described in Example 1. When levamisole was added to the substrate solution, the inhibitor acted in the measuring step (3).

The results (measured values) are shown in Table 4. Further, the ratio (S/N) of the positive control (S) to the negative control (N) in each sample, the ratio (b/a) of the whole blood sample (b) to the plasma sample (a) in each condition, and the ratio of each whole blood sample (b) to the whole blood negative control (without levamisole) or the whole blood positive control (without levamisole) were calculated, and the results are shown in Table 4.

TABLE 4

| levamisole (0.2 mM) | Magnetic particles | – | | – | | + | |
| --- | --- | --- | --- | --- | --- | --- | --- |
| | Substrate (CDP-star) | – | | + | | + | |
| Sample | | Plasma (a) | Whole blood (b) | Plasma (a) | Whole blood (b) | Plasma (a) | Whole blood (b) |
| Negative control (N) | | 663 | 10249 | 708 | 1705 | 808 | 1883 |
| Positive control (S) | | 88346 | 120690 | 84776 | 113017 | 78622 | 95856 |
| S/N | | 133.3 | 11.8 | 119.7 | 66.3 | 97.3 | 50.9 |
| Negative control b/a | | | 15.46 | | 2.41 | | 2.33 |
| Positive control b/a | | | 1.37 | | 1.33 | | 1.22 |
| b/[levamisole (−) whole blood negative control] | | | 1.00 | | 0.17 | | 0.18 |
| b/[levamisole (−) whole blood positive control] | | | 1.00 | | 0.94 | | 0.79 | s a result, it was found that the increased background caused by an endogenous ALP in whole blood samples or hemolized samples was suppressed by the addition of levamisole. Further, the effect was remarkable when levamisole was added to the substrate solution, in comparison with the addition to the solution of magnetic particles. Furthermore, the addition of levamisole did not cause a decreased reactivity in the positive control, and did not adversely affect the ALP used as the label. The addition of levamisole to both the solution of magnetic particles and the substrate solution did not show a remarkable synergistic effect, and it was found that the addition to the substrate solution was important.

Example 4

Analysis of Levamisole Effect Using Patient Samples

The effect of levamisole on the increased background in whole blood samples was shown in Example 3. In this example, samples derived from patients were used to carry out a positive-negative judgment, and the reliability of the obtained results was analyzed.

As samples, whole blood samples and plasma samples derived from healthy persons (6 persons) and cTnI-positive patients (6 persons) were used. Each whole blood was collected by using blood collection tubes containing heparin. The whole blood samples (12 samples) and the plasma samples obtained by centrifuging the whole blood samples were measured. The measurement was carried out using the automated immunoanalyzer and the reagent kit for measuring cTnI including the second antibody labeled with ALP, as described in Example 3, except that the substrate solution supplemented with 0.4 mM levamisole was used.

After the measurement, each cTnI concentration was calculated from the count of luminescence in accordance with a standard curve. As to the whole blood samples, compensation by each hematocrit value (Hct value) was carried out. The result of 6 samples from healthy persons is shown in Table 5, and the result of 6 samples from cTnI-positive patients is shown in Table 6. The case of less than the lower limit (<0.05) was judged as the negative, and the case in which the measured value was obtained was judged as the positive.

TABLE 5

| | Samples from healthy persons | | | | | |
|---|---|---|---|---|---|---|
| | 1 | 2 | 3 | 4 | 5 | 6 |
| Plasma (ng/mL) | <0.05 | <0.05 | <0.05 | <0.05 | <0.05 | <0.05 |
| Hct value (%) | 39.6 | 42.9 | 44.6 | 37.4 | 39.2 | 38.3 |
| Whole blood (ng/mL) Hct compensation | <0.05 | <0.05 | <0.05 | <0.05 | <0.05 | <0.05 |

TABLE 6

| | cTnI abnormal samples | | | | | |
|---|---|---|---|---|---|---|
| | 1 | 2 | 3 | 4 | 5 | 6 |
| Plasma (ng/mL) | 0.05 | 0.58 | 20.61 | 0.05 | 1.71 | 0.16 |
| Hct value (%) | 42.9 | 19.5 | 30.8 | 41.3 | 38.7 | 33.6 |
| Whole blood (ng/mL) Hct compensation | 0.06 | 0.52 | 17.94 | 0.05 | 1.73 | 0.15 |

With respect to the samples from healthy persons, no sample showed a nonspecific high value when either of the whole blood samples or the plasma samples were used, and all samples were judged as negative (see Table 5). With respect to the samples from cTnI-positive patients, all samples were judged as positive, and the measured values of the whole blood sample accorded with those of the plasma samples (see Table 6).

The result shows that even if whole blood is used as a sample, an accurate measurement can be carried out by adding levamisole to a substrate solution, as is the case with a plasma sample.

Example 5

Examination of Levamisole Concentration on Stability of Substrate

In this example, a substrate solution containing CDP-Star and levamisole was used to examine the stability of CDP-Star.

Figure 1:
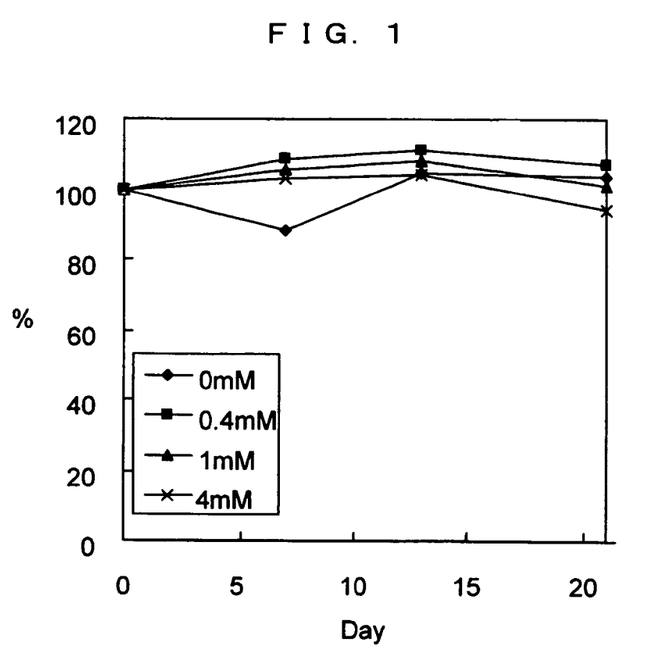
FIG. 1 is a graph showing the remaining activity of CDP-Star in substrate solutions containing levamisole at various concentrations and kept at 4° C.
Figure 2:
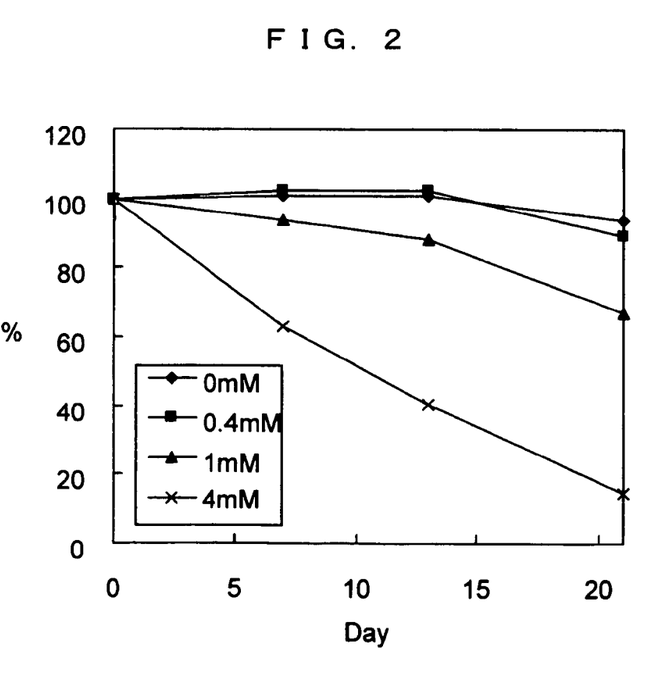
FIG. 2 is a graph showing the remaining activity of CDP-Star in substrate solutions containing levamisole at various concentrations and kept at 25° C.
Figure 3:
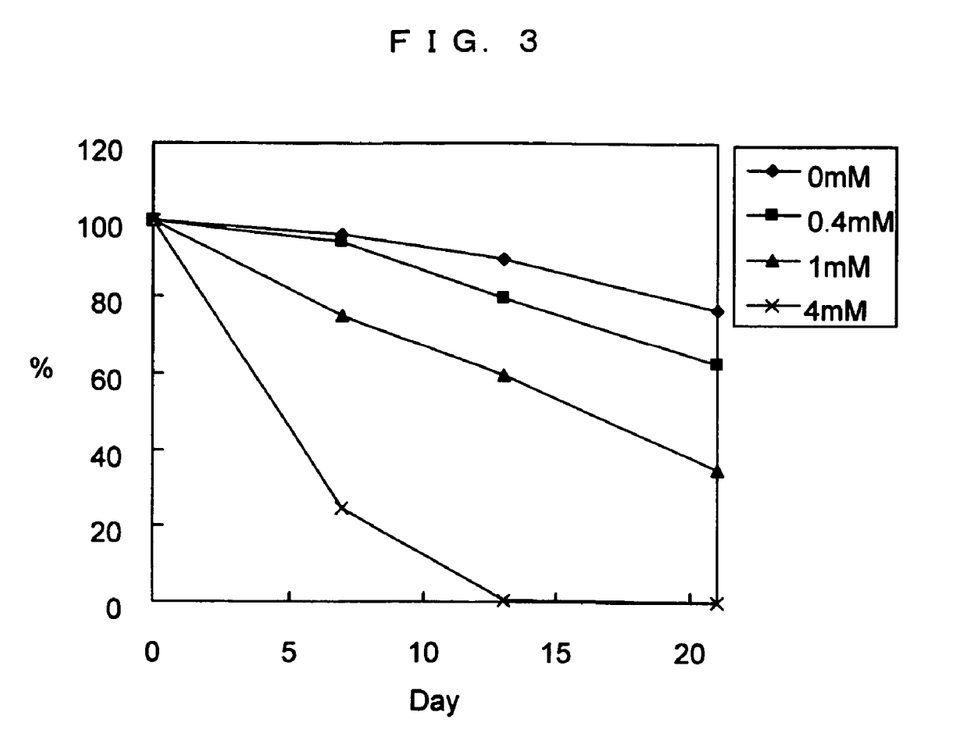
FIG. 3 is a graph showing the remaining activity of CDP-Star in substrate solutions containing levamisole at various concentrations and kept at 37° C.

To a solution containing 0.4 mM CDP-Star, levamisole was added to final concentrations of 0.4, 1.0 and 4.0 mM to prepare substrate solutions to be examined. As a control, a substrate solution containing 0.4 mM CDP-Star without levamisole was used. Each solution was kept at 4, 25, and 37° C. for 3 weeks, and each remaining activity was measured. The results are shown in FIGS. 1 to 3.

Further, the substrate solutions containing 0.4 mM levamisole and kept at 4° C. and 37° C. for 3 weeks were used to confirm the inhibitory effect of levamisole. The result is shown in Table 7.

TABLE 7

| Conditions | Control (levamisole-free) | Levamisole (0.4 mM) |
|---|---|---|
| 4° C., 3 weeks | 32131 | 4086 |
| 37° C., 3 weeks | 34578 | 2920 |

INDUSTRIAL APPLICABILITY

According to the present invention, a whole blood sample can be measured with a decreased background and high accuracy. The effect is more remarkable in, for example, a sensitive chemiluminescent assay using a sensitive substrate for an alkaline phosphatase. Because whole blood can be used as a sample in the present invention, a convenient, rapid, sensitive, and accurate measurement can be carried out, and thus, the present invention is useful for a POCT field or the like.

What we claim is:

1. A method for measuring an analyte present in plasma of a whole blood sample comprising the steps of:
   (1) bringing the whole blood sample into contact with a first substance which is immobilized on an insoluble carrier and which specifically binds to the analyte to be measured and a second substance which is labeled with alkaline phosphatase and which specifically binds to the analyte to be measured, under conditions where hemolysis is substantially avoided, to form a complex comprising first substance-analyte-second substance on the insoluble carrier,
   (2) washing the insoluble carrier with a washing liquid to remove unbound second substance, and
   (3) measuring said complex on the basis of an enzyme reaction of the alkaline phosphatase with an alkaline phosphatase substrate with the addition of an inhibitor of endogenous alkaline phosphatase, the measuring step (3) being carried out in the presence of the inhibitor of endogenous alkaline phosphatase.

2. The method according to claim 1, wherein the inhibitor of endogenous alkaline phosphatase is selected from the group consisting of levamisole, tetramisole, homoarginine, and a derivative thereof.

3. The method according to claim 2, wherein the inhibitor of an endogenous alkaline phosphatase is contained in a solution of a substrate for the alkaline phosphatase used as the label.

4. The method according to claim 2, wherein the substrate is a 1,2-dioxetane-based compound or an acridan-phosphate-based compound.

5. The method according to claim 3, wherein the endogenous alkaline phosphatase is derived from a blood cell.

6. The method according to claim 4, wherein the endogenous alkaline phosphatase is derived from a blood cell.

7. The method according to claim 2, wherein the endogenous alkaline phosphatase is derived from a blood cell.

8. The method according to claim 1, wherein the inhibitor of an endogenous alkaline phosphatase is contained in a solution of a substrate for the alkaline phosphatase used as the label.

9. The method according to claim 1, wherein the substrate is a 1,2-dioxetane-based compound or an acridan-phosphate-based compound.

10. The method according to claim 9, wherein the endogenous alkaline phosphatase is derived from a blood cell.

11. The method according to claim 8, wherein the endogenous alkaline phosphatase is derived from a blood cell.

12. The method according to claim 1, wherein the endogenous alkaline phosphatase is derived from a blood cell.

13. The method according to claim 1, wherein the contacting step (1) is carried out in the presence of a detergent at a concentration that does not cause substantial hemolysis.

14. The method according to claim 13, wherein the insoluble carrier is a magnetic particle, and the removal step (2) is carried out by a magnetic bound/free separation.

15. The method of claim 13 wherein said detergent is selected from the group consisting of polyoxyethylene sorbitan-based detergents and sulfobetaine-based detergents.

16. The method of claim 15, wherein said detergent is chosen from the group consisting of polyoxyethylene sorbitan monolaurate and polyoxyethylene sorbitan monooleate.

17. The method according to claim 1, wherein the insoluble carrier is a magnetic particle, and the removal step (2) is carried out by a magnetic bound/free separation.

18. A reagent kit for measuring an analyte present in plasma of a whole blood sample, comprising
    (1) a first substance which is immobilized on an insoluble carrier and specifically binds to the analyte in the plasma portion of the whole blood which is to be measured,
    (2) a second substance which is labeled with an alkaline phosphatase and specifically binds to the analyte to be measured, and
    (3) an inhibitor of an endogenous alkaline phosphatase which is contained in a solution of a substrate for the alkaline phosphatase used as the label.

* * * * *